(12) United States Patent
Yao et al.

(10) Patent No.: US 9,884,046 B1
(45) Date of Patent: Feb. 6, 2018

(54) METHOD OF TREATING LUNG CANCER

(71) Applicant: Macau University of Science and Technology, Macau (CN)

(72) Inventors: Xiao Jun Yao, Macau (CN); Lai Han Elaine Leung, Macau (CN); Liang Liu, Macau (CN); Xing Xing Fan, Macau (CN); Chun Xie, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

(21) Appl. No.: 15/632,406

(22) Filed: Jun. 26, 2017

(51) Int. Cl.
*A61K 31/428* (2006.01)
*C07D 277/72* (2006.01)
*G01N 33/574* (2006.01)
*C07K 14/47* (2006.01)
*C12Q 1/68* (2006.01)
*G01N 33/68* (2006.01)
*A61K 38/00* (2006.01)

(52) U.S. Cl.
CPC .......... *A61K 31/428* (2013.01); *C07D 277/72* (2013.01); *C07K 14/47* (2013.01); *C12Q 1/6886* (2013.01); *G01N 33/57423* (2013.01); *G01N 33/57484* (2013.01); *A61K 38/00* (2013.01); *C07K 2319/00* (2013.01); *C12Q 2600/112* (2013.01); *G01N 33/574* (2013.01); *G01N 33/68* (2013.01)

(58) Field of Classification Search
CPC ................ C07D 277/72; A61K 31/428; G01N 33/57423; G01N 33/57484
See application file for complete search history.

(56) References Cited

FOREIGN PATENT DOCUMENTS

WO    WO-0059878 A2 * 10/2000    .......... C07C 323/09

OTHER PUBLICATIONS

Almoguera, C., et al. (1988). Most Human Carcinomas of the Exocrine Pancreas Contain Mutant c-K-ras Genes. Cell, 53, 549-554.
Bos, J.L. (1989). ras Oncogenes in Human Cancer: A Review. Cancer Research, 49, 4682-4689.
Burns, M.G., et al. (2014). Approach for targeting Ras with small molecules that activate SOS-mediated nucleotide exchange. PNAS, 111(9), 3401-3406.
Chang, E.H., et al. (1982). Human genome contains four genes homologous to transforming genes of Harvey and Kirsten murine sarcoma viruses. Proc. Natl. Acad. Sci. USA, 79, 4848-4852.
Cox, A.D., et al. (2014). Drugging the undruggable RAS: Mission Possible? Nature Reviews, 13, 828-851.
Forbes, S., et al. (2006). COSMIC 2005. British Journal of Cancer, 94, 318-322.
Hancock, J.F., et al. (2005). Ras plasma membrane signalling platforms. Biochemical Journal. 389, 1-11.
Maurer, T., et al. (2012). Small-molecule ligands bind to a distinct pocket in Ras and inhibit SOS-mediated nucleotide exchange activity. PNAS, 109(14), 5299-5304.
McCormick, F. (2015). KRAS as a Therapeutic Target. Clinical Cancer Research 21(8), 1797-1801.
Rajalingam, K., et al. (2007). Ras oncogenes and their downstream targets. Biochimica et Biophysica Acta, 1773, 1177-1195.
Pylayeva-Gupta, Y., et al. (2013), RAS oncogenes: weaving a tumorigenic web. Nature Reviews Cancer, 11(11), 1-29.
Reddy, E.P., et al. (1982). A point mutation is responsible for the acquisition of transforming properties by the T24 human bladder carcinoma oncogene. Nature, 300, 149-152.
Rich, R.L., et al. (2007). Higher-throughput, label-free, real-time molecular interaction analysis. Analytical Biochemistry, 361, 1-6.
Santos, E., et al. (1984). Malignant Activation of a K-ras Oncogene in Lung Carcinoma but Not in Normal Tissue of the Same Patient. Science, 223, 661-664.
Shaw, R.J., et al. (2006). Ras, PI(3)K and mTOR signalling controls tumour cell growth. Nature, 441, 424-430.
Spiegel, J., et al. (2014). Small-molecule modulation of Ras signaling. Nature Chemical Biology, 10, 1-10.
Sunaga, N., et al. (2012) Oncogenic KRAS-induced interleukin-8 overexpression promotes cell growth and migration and contributes to aggressive phenotypes of non-small cell lung cancer. International Journal of Cancer, 130(8), 1-20.
Tabin, C.J., et al. (1982). Mechanism of activation of a human oncogene. Nature, 300, 143-149.

* cited by examiner

*Primary Examiner* — Michael Barker
(74) *Attorney, Agent, or Firm* — Eagle IP Limited; Jacqueline C. Lui

(57) ABSTRACT

One embodiment relates to a method of treating lung cancer by administering a compound of formula I to a patient. Another embodiment relates to a method of treating cancer with a KRAS mutation that includes administering to a patient the compound with the following formula I:

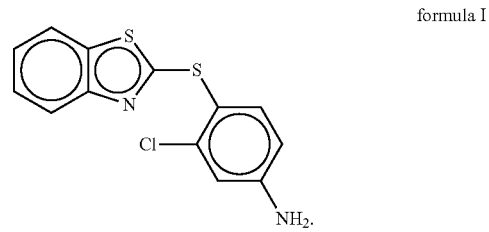

formula I

20 Claims, 9 Drawing Sheets
(5 of 9 Drawing Sheet(s) Filed in Color)

METHOD OF TREATING LUNG CANCER

FIELD OF THE INVENTION

The present invention relates to a method of treating lung cancer. In particular, the present invention relates to a method of treating non-small cell lung cancer (NSCLC).

BACKGROUND

Cancer is a disease involving abnormal cell growth with the potential to invade or spread to other areas of the body. Lung cancer starts when cells of the lung become abnormal and proliferate uncontrollably. There are two main types of lung cancer, namely, non-small cell lung cancer (NSCLC) and small cell lung cancer.

In view of the demand for effectively treating lung cancer in a patient, particularly NSCLC, improvements in method and compositions that treat lung cancer are desired.

SUMMARY

One example embodiment is a method of treating non-small cell lung cancer (NSCLC) in a patient. The method includes administering to the patient a therapeutically effective amount of a compound of formula I to treat the NSCLC as follows:

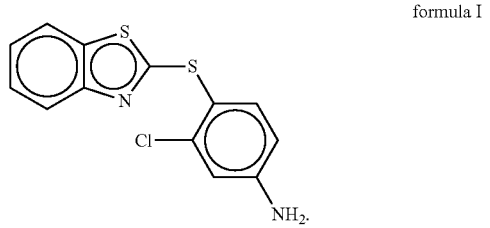

formula I

Another example embodiment is a method of inhibiting progress of tumor growth in a patient with cancer of which tumor cells have or express a mutant Kirsten rat sarcoma 2 viral oncogene homolog (KRAS) The method includes administering the compound of formula I to the patient to treat the cancer.

Other example embodiments are discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
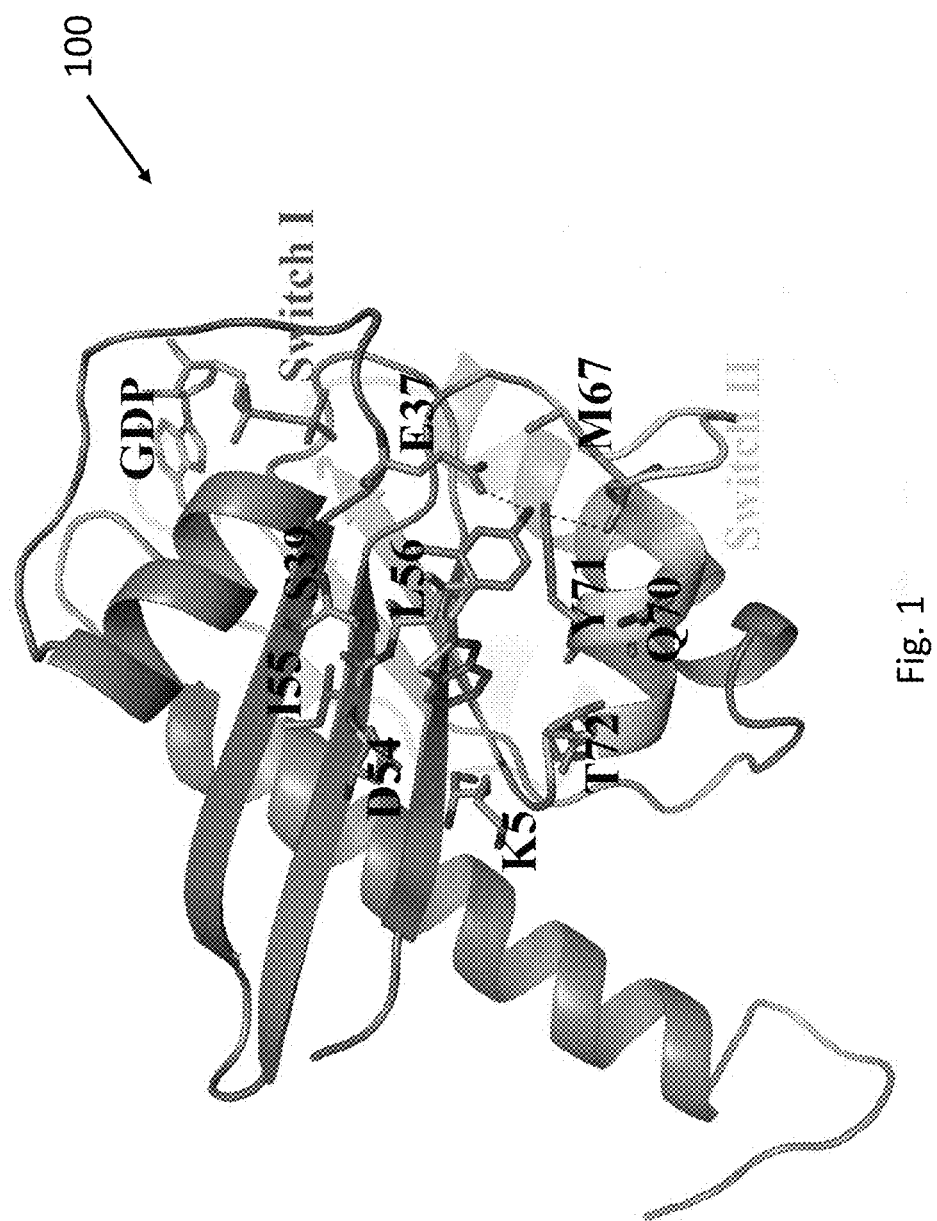
FIG. 1 shows a binding mode between a compound of formula I (i.e. compound 0375-0604) and Kirsten rat sarcoma 2 viral oncogene homolog (KRAS) in accordance with an example embodiment.

Example embodiments relate to methods to treat non-small cell lung cancer (NSCLC) in a patient by administering, to the patient, a therapeutically effective amount of a compound with the following formula I:

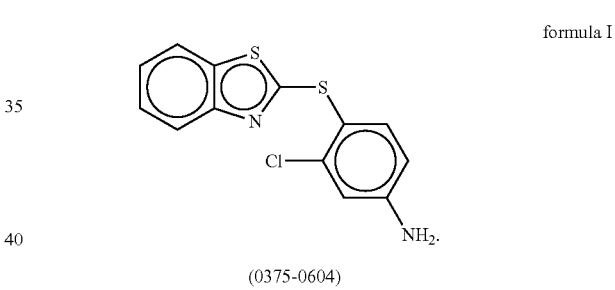

formula I (0375-0604)

Example embodiments relate to a method to treat lung adenocarcinoma in a patient, and the method includes administering a therapeutically effective amount of the compound of formula I to the patient.

Example embodiments relate to a method of inhibiting progress of tumor growth in a patient with cancer, and the method includes diagnosing the patient with the cancer when the presence of a mutation of KRAS in cancer cells is detected. The method also includes administering a therapeutically effective amount of the compound of formula I to the patient with the cancer to inhibit the progress of tumor growth. Tumor cells of the cancer include, express or have a mutant Kirsten rat sarcoma 2 viral oncogene homolog (KRAS).

In one example embodiment, tumor cells or cancer cells express, have or include a mutant KRAS. In a further embodiment for example, the mutant KRAS includes an amino acid substitution from glycine (G) to cysteine (C) at codon 12 (G12C mutation). In yet another example embodiment, the mutant KRAS includes an amino acid substitution from glutamine (Q) to histidine (H) at position or codon 61 in the KRAS (Q61H mutation). In yet another example embodiment, the mutant KRAS includes Q61H and G12C mutations.

In one example embodiment, a mutant KRAS causes an increased level of guanosine-5'-triphosphate (GTP)-bound KRAS in cancer cells, and the compound of formula I inhibits the level of GTP-bound KRAS to treat the disease.

In one embodiment for example, a mutant KRAS activates phosphorylation of CRAF in cancer cells, and the compound of formula I inhibits the phosphorylation of the CRAF to treat the disease.

KRAS belongs to a family of GTPases and is a member of the RAS (Rat Sarcoma) protein group. Full-length KRAS features a C-terminal domain. The C-terminal domain contains a unique stretch directly associated with the cytoplasmic membrane. KRAS is a small GTPase that normally alternates between a GTP-bound active state and a GDP-bound inactive state. KRAS stimulates signaling pathways and promotes tumorigenesis. Mutationally activated KRAS gene was detected in human cancers. 90% of KRAS mutations were found in lung adenocarcinoma. It is desirable to develop KRAS inhibitors to inhibit proliferation of cancer cells with KRAS mutation.

In one example embodiment, the compound of formula I binds with KRAS, and inhibits proliferation of NSCLC cell lines. In one example embodiment, the compound of formula I decreases cell viability of cancer cells with a KRAS mutation, and decreases an increased level of phosphorylation of CRAF that has resulted from mutated KRAS. In another example embodiment, the compound of formula I inhibits the level of GTP-bound KRAS in KRAS mutant cells.

Example 1

Material and Methods
1. Molecular Docking

The KRAS structure (PDB code: 4DSU) complexed with guanosine diphosphate (GDP) and a benzimidazole (BZIM) compound was used for the modeling of possible binding mode between compound 0375-0604 and KRAS. The crystal structure was prepared in the Prep Wiz module in Maestro (Version 9.1, Schrodinger) with GDP, and water molecules within 5 Å of the groups were kept. A grid file was generated based on the position of ligand BZIM in the Grid Generation wizard for docking. Compound 0375-0604 was preprocessed and optimized by the LigPrep module with OPLS-2005 force field. Finally, the docking process was performed in the Glide Docking module based on the previous obtained grid file using an extra precision (XP) protocol followed by a post-docking minimization using MM-GBSA method.

2. Bio-Layer Interferometry

The interaction between KRAS and compound 0375-0604 was determined by bio-layer interferometry using an Octet Red 96 instrument (FortéBio Inc.). Ni-NTA Biosensors tips (FortéBio, Inc., Menlo Park, Calif.) were prewetted with PBS to establish a baseline before immobilization. His-KRAS was then immobilized onto Ni-NTA Biosensors. The experiments comprised five steps: (1) baseline acquisition, (2) KRAS loading onto the sensor, (3) second baseline acquisition, (4) association of compound 0375-0604 for the measurement of kon, and (5) dissociation of compound 0375-0604 for the measurement of koff. Six concentrations of compound 0375-0604 were used for detection. The association and dissociation plot and kinetic constants were obtained with FortéBio data analysis software. Equilibrium dissociation constants (Kd) were calculated in the ratio of $k_{off}$ to $k_{on}$.

3. Cell Culture and 3-(4,5-Dimethylthiazol-2-Yl)-2,5-Diphenyltetrazolium Bromide (MTT) Assay H2122, H460 and H358 cells were purchased from ATCC and cultivated with Roswell Park Memorial Institute (RPMI) 1640 medium supplemented with 10% fetal bovine serum (Gibco, Big Cabin, Oklahoma, Me., USA), 100 U/mL penicillin and 100 μg/mL streptomycin (Gibco, Big Cabin, Oklahoma, Me., USA). All the cells were cultivated at 37° C. with 5% $CO_2$ incubator. Cells were seeded on a 96-well microplate with 3000, 4000 or 5000 cells/well, and were cultured overnight for cell adhesion. Different concentrations of compound 0375-0604 were added to the microplates, and the plates were incubated for 24, 48 or 72 h. Each dosage was repeated as triplicate. 10 μL MTT (5 mg/mL) solution was added to every well. After incubation for 4 h, 100 μL dimethyl sulfoxide (DMSO) was added to each well. After shaking for 15 min, the absorbance of the plate was measured at 570 nm (absorbance) and 650 nm (reference) by a microplate reader (Tecan, Morrisville, N.C., USA).

4. Western Blot Analysis

After treatment with compound 0375-0604 for 24 h, 48 h or 72 h, radioimmunoprecipitation assay (RIPA) lysis buffer which contains protease and phosphatase inhibitors, was added to extract the whole cell protein. Bio-Rad DC™ protein assay kit (Bio-Rad, Philadelphia, Pa., USA) was used to quantify the protein. 30 μg protein lysate were loaded and separated by 10% sodium dodecyl sulfate (SDS)-polyacrylamide gel electrophoresis and transferred to a nitrocellulose (NC) membrane. The membranes were incubated with the primary antibody (1:2000) and then with a fluorescence-conjugated secondary antibody (1:10000). Glyceraldehyde 3-phosphate dehydrogenase (GAPDH) was used as the loading control for normalization. The signal of the membranes was scanned with a LI-COR Odyssey Scanner (Belfast, Me., USA).

5. RAS Binding Domain Pull Down

RAS activity was detected using the RAS Activation Assay Kit from Upstate-Millipore. The whole cell lysates were incubated with Glutathione S-transferase-Rho-binding domain (GST-RBD) and glutathione beads for 1 h. Agarose beads were pelleted by centrifugation and washed 3 times with $Mg^{2+}$ lysis buffer. Agarose beads were re-suspended in loading buffer. Samples were analyzed by the western blotting as previously described and blots probed using anti-KRAS antibody (sc-30, SANTA).

6. Cell Cycle Analysis

H358 cells were plated with $2.0 \times 10^5$ cells/well at a 6-well plate and cultured overnight for attachment. After treatment with compound 0375-0604 at 0, 50, 100 μM for 24 h, all cells were harvested by trypsin, and centrifuged at 1000 rpm, at room temperature for 5 min. Cells pellets were re-suspended in 70% ethanol at 4° C. for 30 min. Cells were centrifuged at 1000 rpm for 5 min to remove all the ethanol. Each cell pellet was re-suspended in 300 μL Propidium iodide (PI) staining solution at 37° C. for 30 min in the dark. The cells were then washed twice with phosphate-buffered saline (PBS). Finally, cells were re-suspended in 300 μL PBS and transferred to the flow cytometer (BD FACS Aria III).

7. Statistical Analysis

Descriptive analytical data are presented as means±SEM. Statistical analysis was conducted using Graph Prism 5.0. Significant differences between datasets were assessed by one-way analysis of variance (ANOVA).

Example 2

1. The Binding Mode Between Compound 0375-0604 and KRAS

Molecular docking calculations were performed to study the binding mode between compound 0375-0604 and KRAS. The docking results 100 were displayed in FIG. 1. Compound 0375-0604 is displayed in sticks with carbon atoms colored slate. Residues formed from direct interactions with the ligand was shown in green carbons. The son of sevenless homolog 1 (SOS 1) protein was represented in slate cartoons. Compound 0375-0604 binds to KRAS with a moderate binding free energy of −49.21 kcal/mol and glide docking of −4.27 kcal/mol. Compound 0375-0604 is located in a binding pocket that is mainly composed of residues of switch I and switch II and interacted with residues lining the pocket. The two ring groups inserted to the binding pocket with the linker atom were exposed to solvent environment. The ligand amino acid formed H-bonds interaction with the backbone of Met67 and the side chain of Glu37 which are located in switch I and switch II, respectively. At the same time, the ligand formed polar contacts with residues Lys5, Ser39, Arg41, Asp54, Arg68, Gln70 and Thr74. In addition, the hydrophobic contacts formed between the ligand and surrounded residues, including Leu6, Val7, Ile55, Leu56 and Tyr71, further fasten the ligand binding.

2. Binding Affinity of Compound 0375-0604 to KRAS

Figure 2:
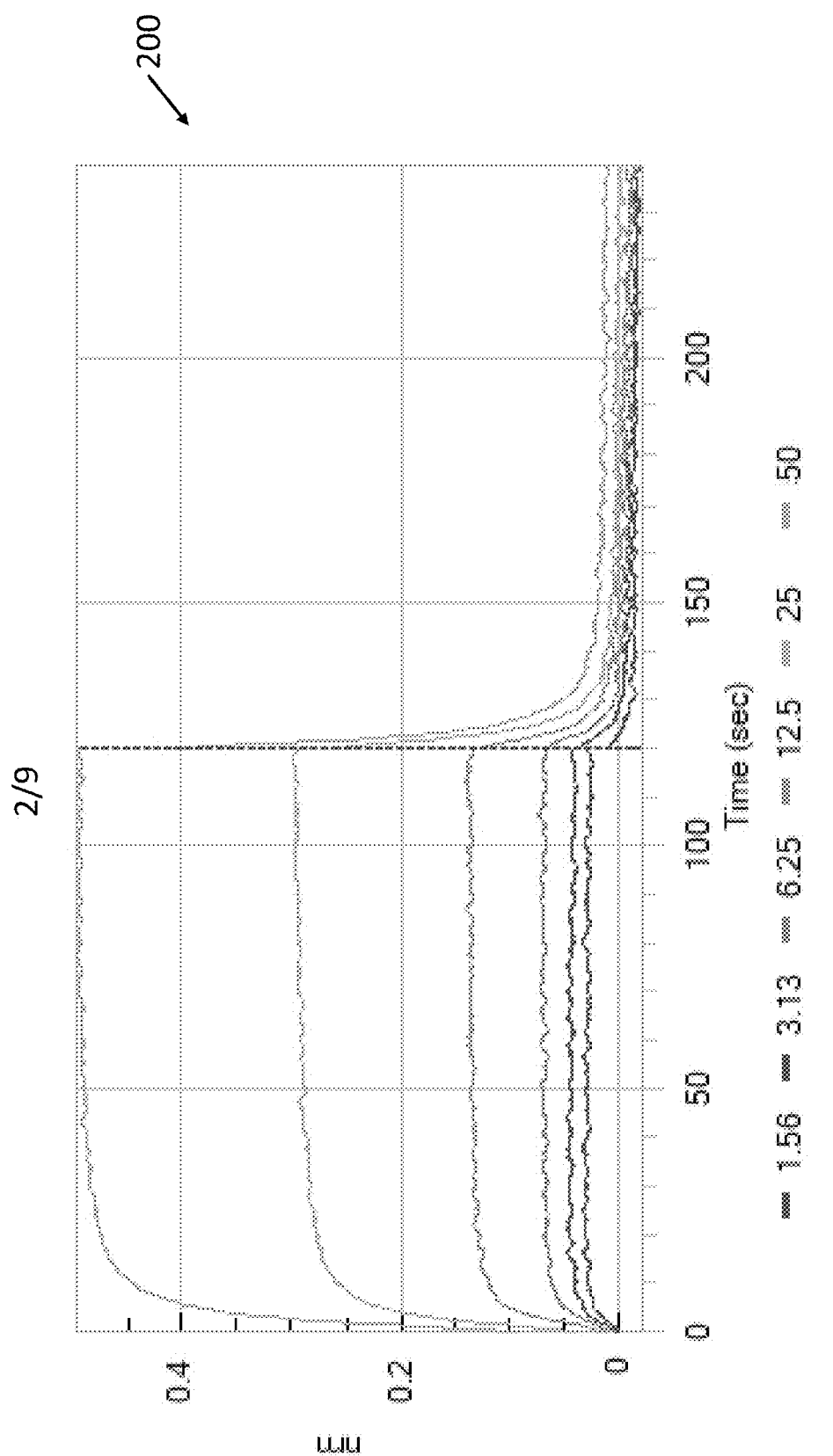
FIG. 2 shows the interaction between KRAS and compound 0375-0604 by bio-layer interferometry assay in accordance with an example embodiment.

Bio-layer interferometry assay (BLI), a label-free technology, was used to measure the biomolecular interaction between KRAS and compound 0375-0604. In this study, the His-labeled KRAS protein was immobilized on the Ni-NTA (NTA) Biosensors. As shown in FIG. 2, the interaction between KRAS protein and compound 0375-0604 with different concentrations was measured. Experimental data for association and dissociation are represented on the left and right side. Concentrations of compound 0375-0604 (μM) were shown to each binding curve (i.e. 1.56, 3.13, 6.25, 12.5, 25, and 50 μM). All the binding curves 200 in FIG. 2 showed very short and fast association/dissociation steps, followed by slower and much longer association/ dissociation steps. The rate constants of $k_{on}=1.83E+04 M^{-1} S^{-1}$ and $k_{off}=2.12E-01 S^{-1}$ resulted in a Kd value of 11.60 μM.

3. Compound 0375-0604 Decreases Cell Viability of NSCLC Cells with KRAS Mutation The cytotoxicity of compound 0375-0604 was determined by MTT assay. The effect of compound 0375-0604 on three NSCLC cell lines, H2122, H358 and H460 was examined. H2122, H358 and H460 are harboring KRAS-activating mutations. H2122 and H358 cells have mutant KRAS that includes an amino acid substitution from a glycine to a cysteine at codon or position 12 (i.e. mutant KRAS $^{G12C}$). H460 cells have mutant KRAS that includes an amino acid substitution from a glutamine to a histidine at codon or position 61 (i.e. mutant KRAS Q61H).

Figure 3B:
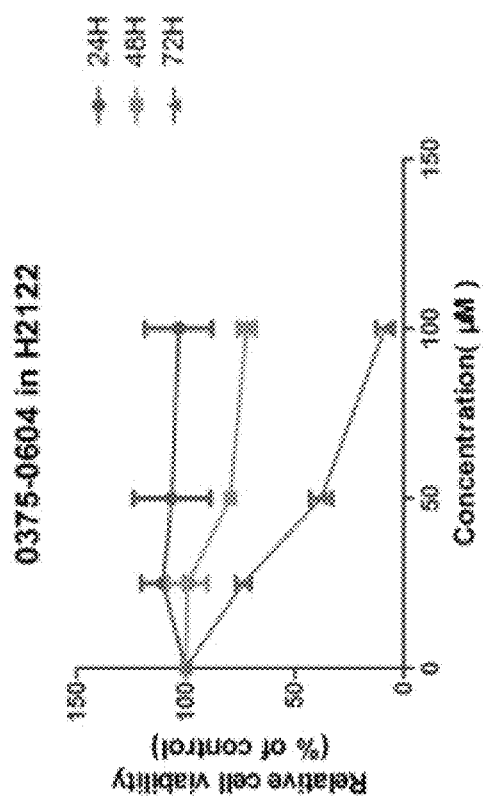
FIG. 3B shows that compound 0375-0604 decreases cell viability in NSCLC cell line H2122 in accordance with an example embodiment.
Figure 3A:
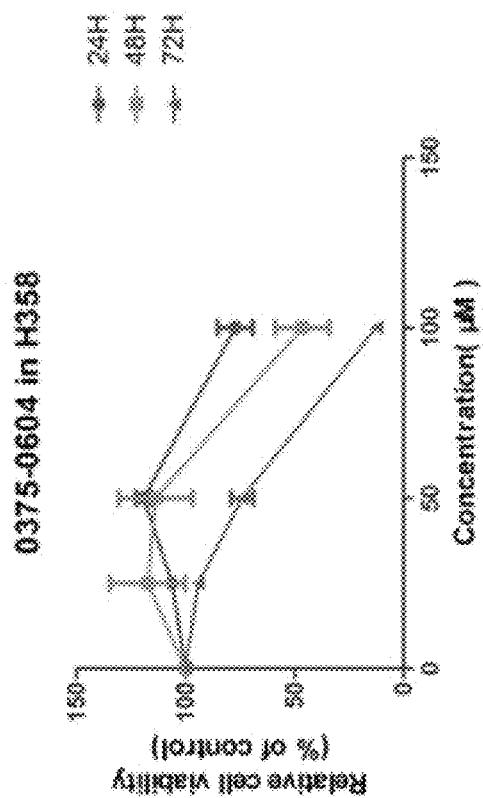
FIG. 3A shows that compound 0375-0604 decreases cell viability in NSCLC cell line H358 in accordance with an example embodiment.
Figure 3C:
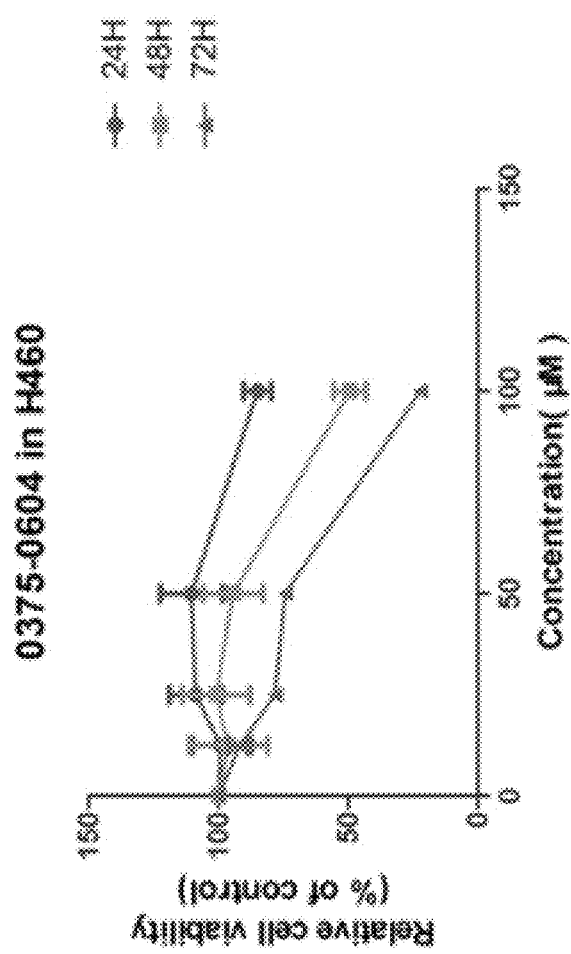
FIG. 3C shows that compound 0375-0604 decreases cell viability in NSCLC cell line H460 in accordance with an example embodiment.

Cells were incubated with compound 0375-0604 at different concentrations (0, 25, 50, 100 μM) for 24, 48, and 72 h. As shown in FIGS. 3A-3C, the cell viability of three NSCLC cell lines was decreased by the treatment of compound 0375-0604 in a dose-dependent and time-dependent manner. The IC50 values of compound 0375-0604 on the three cell lines at 24, 48 and 72 h are shown in Table 1. The results mentioned above suggested that compound 0375-0604 exhibited a significantly cytotoxic effect on NSCLC H2122, H358 and H460 cells. The results also showed that the proliferation of the cancer cells with a G12C mutant KRAS or Q61H mutant KRAS or G12C and Q61H dual mutant KRAS was inhibited by compound 0375-0604.

TABLE 1

The IC$_{50}$ values of compound 0375-0604 on three NSCLC cell lines.

| Cancer cell lines | IC$_{50}$ values (μM) | | |
|---|---|---|---|
| | 24 h | 48 h | 72 h |
| H358 | >100 | >100 | 63.83 ± 3.89 |
| H2122 | >100 | >100 | 39.56 ± 3.09 |
| H460 | >100 | 100.30 ± 13.30 | 66.02 ± 11.82 |

4. Compound 0375-0604 Decreases Phosphorylation of RAS Downstream Signaling

Figure 4:
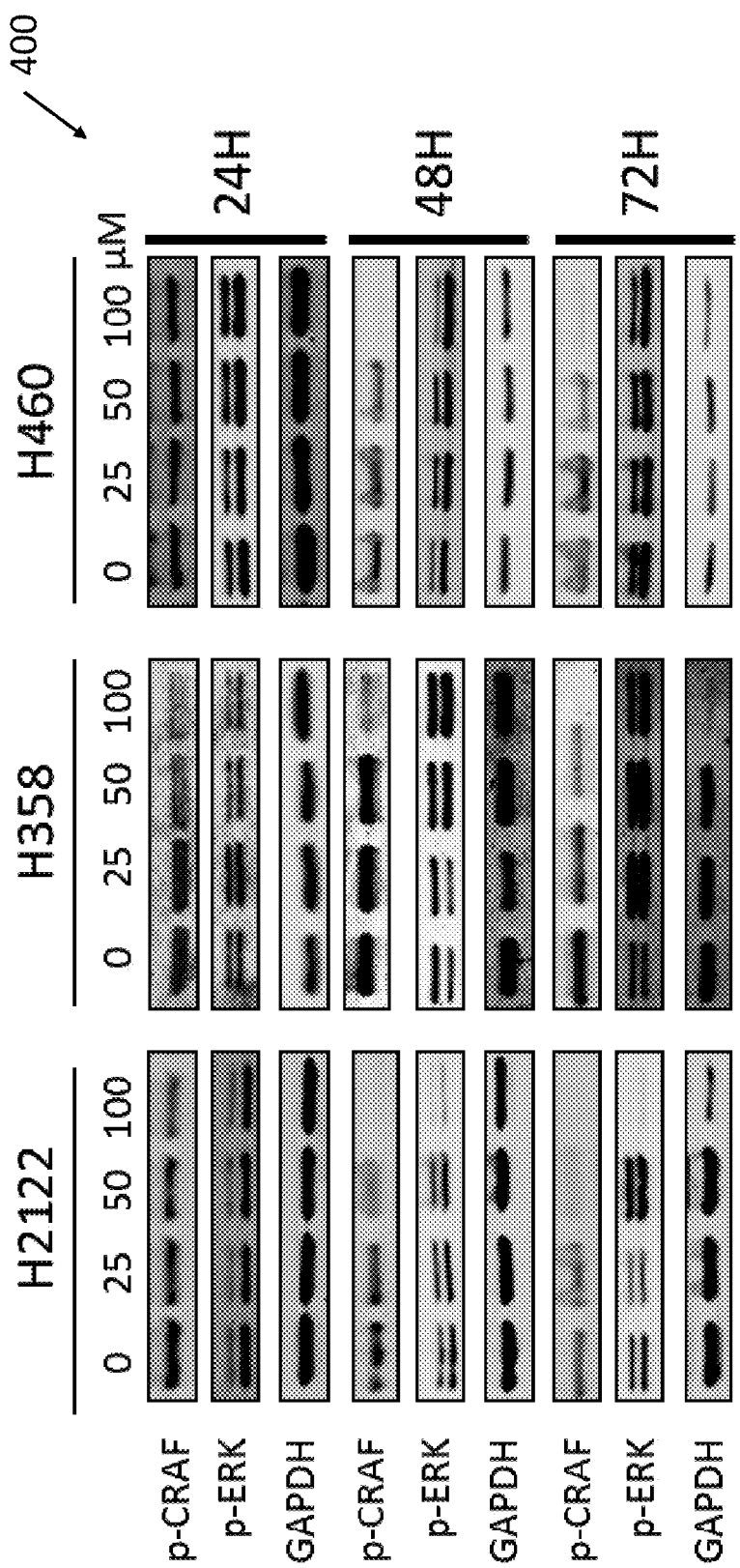
FIG. 4 shows that compound 0375-0604 decreases the level of phosphorylation of Cellular Rapidly Accelerated Fibrosarcoma (p-CRAF) in cell lines H2122, H358 and H460 for 24, 48 and 72 h in accordance with an example embodiment.

FIG. 4 shows the western blot analysis 400 on the effect of compound 0375-0604 on the inhibition of KRAS downstream signaling. Untreated cells were used as control. A representative of at least three independent experiments for each of cell lines is showed. As shown in FIG. 4, the level of phosphorylation of Cellular Rapidly Accelerated Fibrosarcoma (p-CRAF) was decreased in H2122, H460 and H358 cells treated with compound 0375-0604, as compared with the untreated cells. The result shows that compound 0375-0604 can suppress KRAS downstream signaling.

5. Compound 0375-0604 Inhibits the Level of GTP-Bound KRAS

Figure 5:
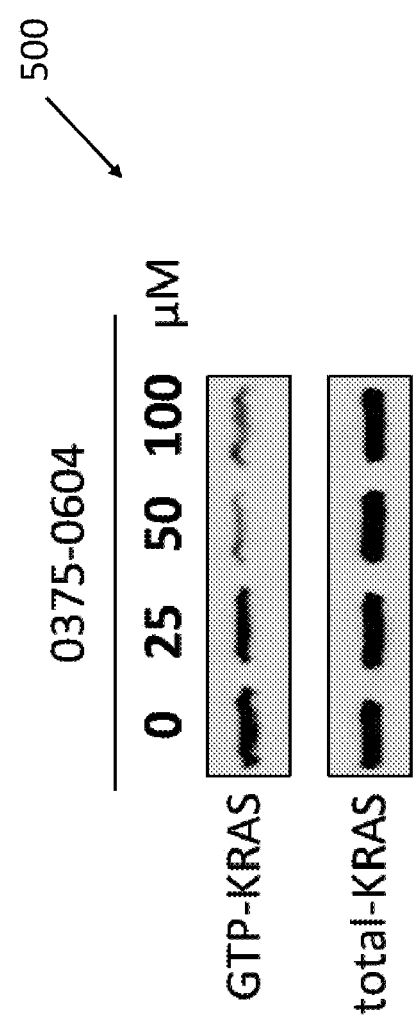
FIG. 5 shows that compound 0375-0604 decreases the level of GTP-bound KRAS in cell lines H358 in accordance with an example embodiment.

KRAS mutant cells (H358) were treated with compound 0375-0604 for 24 h. After 24 h treatment, cells were collected and determined by a RAS-binding domain pull-down (RBD:PD) assay and immunoblotting with a KRAS-specific antibody. The result 500 of the assay in FIG. 5 shows that the level of GTP-bound KRAS was inhibited by the compound at 50 and 100 μM.

6. Compound 0375-0604 Induces Cell Cycle Arrest in H358

Figure 6:
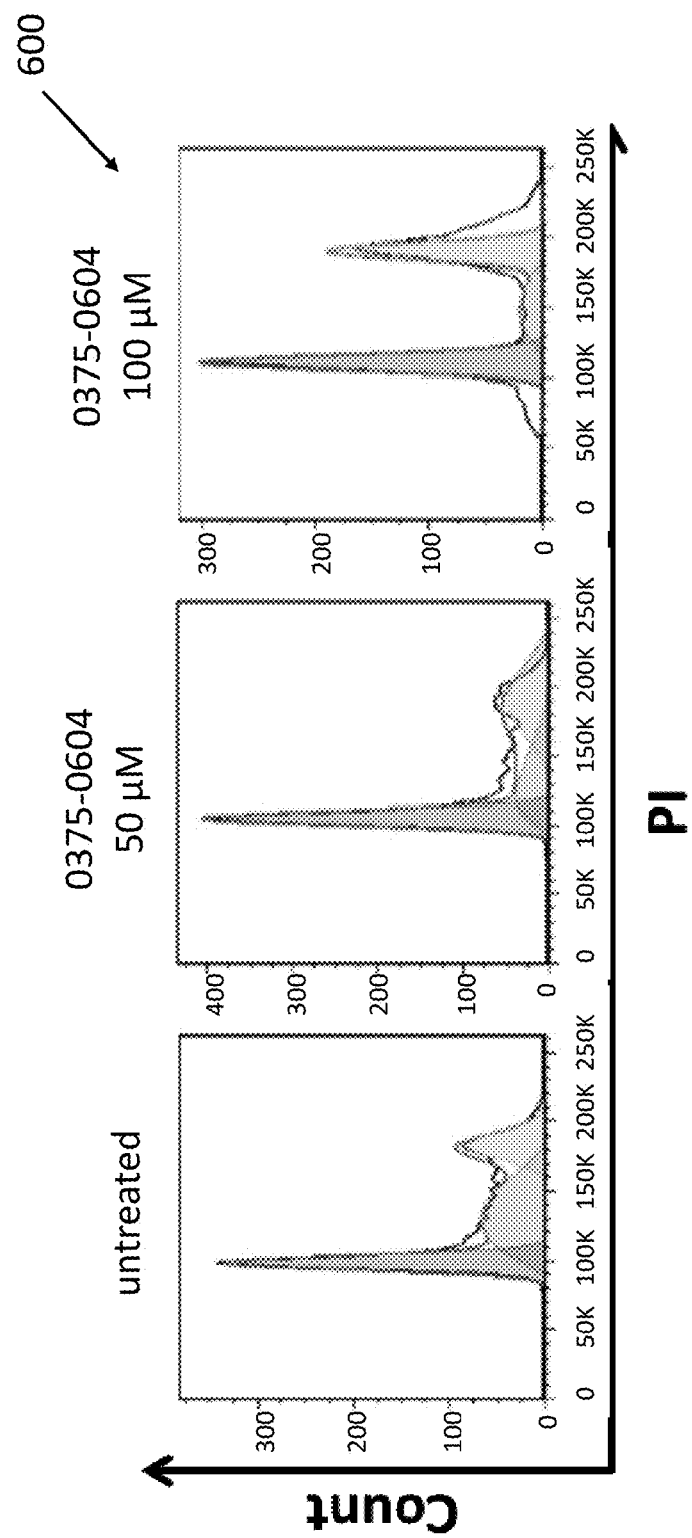
FIG. 6 shows that compound 0375-0604 induces cell cycle arrest in cell line H358 in accordance with an example embodiment.

H358 cells were treated with compound 0375-0604 at different concentrations (0, 50, 100 μM) for 24 h, and stained with Propidium iodide (PI). The samples were analyzed by flow cytometry. The result 600 shows that after 24 h treatment, the percentage of cells in G0/G1 phase slightly decreased while the percentage of cells increased in G2/M phase as shown in FIG. 6. These results indicated that the mechanism through which compound 0375-0604 induced inhibition is G2/M cell cycle arrest in H358 cells in dose-dependent manner.

Therefore, compound 0375-0604 of formula I inhibits the progress of tumor growth such that the compound can be used to treat cancer cells with a KRAS mutation. The mutation can be KRAS $^{G12C}$ mutation or $^{Q61H}$ mutation, or KRAS $^{G12C/Q61H}$ dualmutation. The compound can be used to treat lung cancer, NSCLC or lung adenocarcinoma by inhibiting the level of GTP-bound KRAS and/or decreasing the phosphorylation of CRAF.

Figure 7:
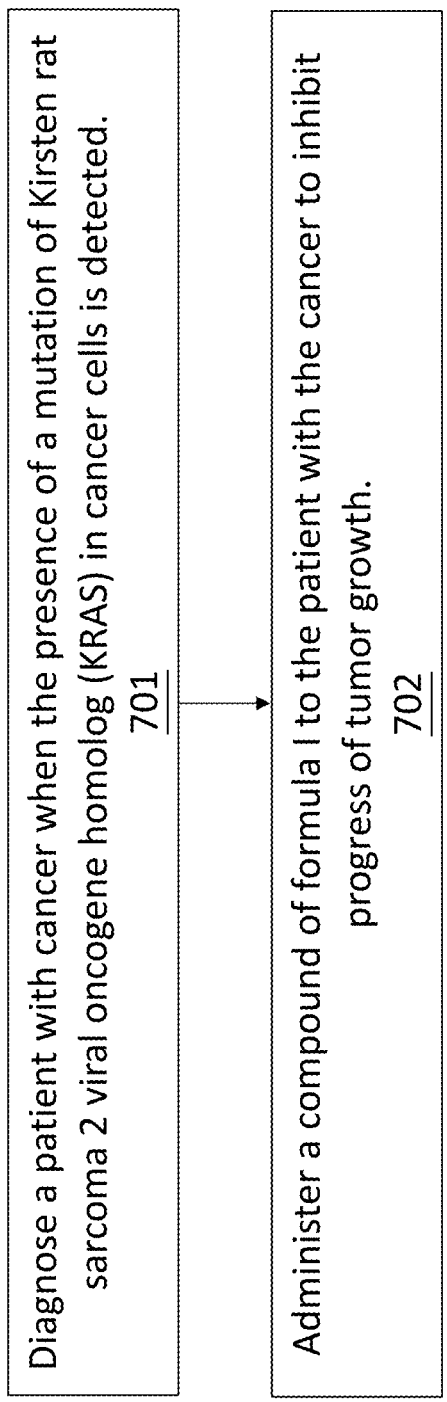
FIG. 7 shows a method to inhibit progress of tumor growth in a patient with cancer in accordance with an example embodiment.

FIG. 7 is a method to inhibit progress of tumor growth in a patient with cancer.

Block 701 states diagnose a patient with cancer when the presence of a mutation of KRAS in cancer cells is detected.

In one example embodiment, a mutation analysis of cancer cells is conducted to detect the presence of a KRAS mutation. In one example embodiment, the mutation analysis can be conducted using methods that include, but are not limited to, one or more of the following: Polymerase Chain Reaction (PCR) to amplify the appropriate region of the KRAS gene and distinguish wild type from mutant sequences, nucleic acid sequencing, allele-specific PCR methods, single-strand conformational polymorphism analysis, melt-curve analysis, probe hybridization, etc.

In a further example embodiment, a mutation analysis of codon 12 and/or 61 in KRAS is conducted. If the cancer patient has a mutant KRAS at codon 12 resulting from amino acid substitution of glycine (G) to cysteine (C), the patient will be diagnosed as having cancer cells with mutant KRAS $^{G12C}$. If the cancer patient has a mutant KRAS at codon 61 resulting from amino acid substitution of glutamine (Q) to histidine (H), the patient will be diagnosed as having cancer cells with mutant KRAS $^{Q61H}$.

Block 702 states administer the compound of formula I to the patient with the cancer to inhibit progress of tumor growth.

In an example embodiment, the compound is administered directly or in the form of pharmaceutical compositions with suitable carriers or excipients. In one example embodiment, suitable routes of administration may, for example, include oral, rectal, transmucosal, nasal, or intestinal administration and parenteral delivery. The compound or the pharmaceutical composition that includes the compound can be administered locally. For example, the compound can be delivered via injection or in a targeted drug delivery system, such as a depot or sustained release formulation.

Figure 8:
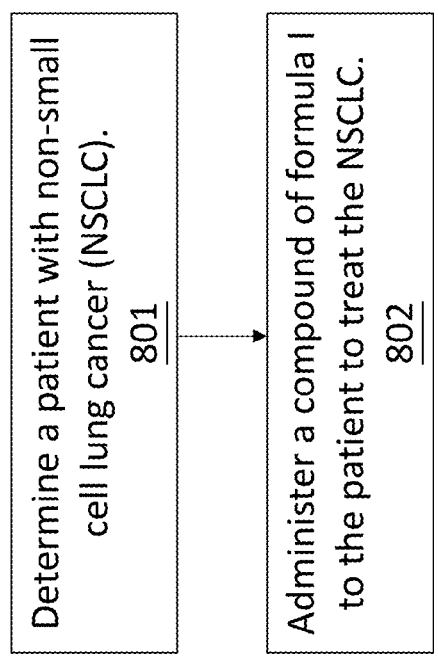
FIG. 8 shows a method to treat NSCLC in a patient in accordance with an example embodiment.

FIG. 8 is a method to treat NSCLC in a patient.

Block 801 states determine a patient with NSCLC. In one example embodiment, it can be determined whether the patient suffers from NSCLC using methods such as chest X-ray, multi-detector computerized tomography scan, magnetic resonance imaging, positron emission tomography, fine and core needle biopsies of the lung, bronchoscopy, endobronchial ultrasound, navigational bronchoscopy, etc.

Block 802 states administer the compound of formula I to the patient to treat the NSCLC.

In one example embodiment, the compound is administered directly or in pharmaceutical compositions along with suitable carriers or excipients. In one example embodiment, suitable routes of administration may, for example, include oral, rectal, transmucosal, nasal, or intestinal administration and parenteral delivery. The compound or the pharmaceutical composition that includes the compound can be administered locally. For example, the compound can be delivered via injection or in a targeted drug delivery system, such as a depot or sustained release formulation. In one example embodiment, the compound is administered in conjunction with administration of other chemo-drug that treats NSCLC such as Tarceva, etc.

Figure 9:
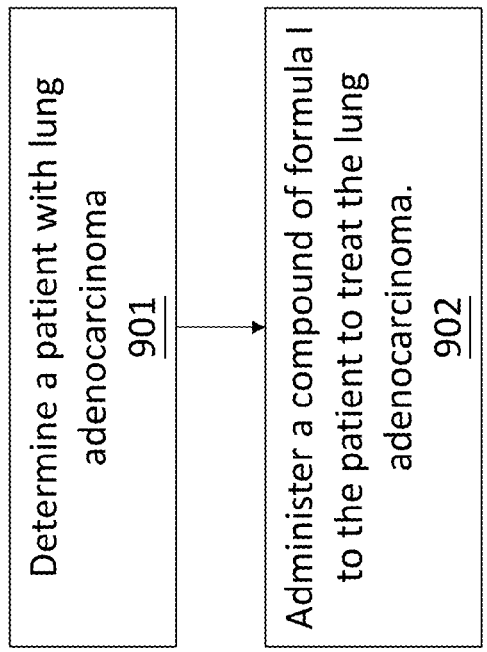
FIG. 9 shows a method to treat lung adenocarcinoma in a patient in need of treatment of the lung adenocarcinoma in accordance with an example embodiment.

FIG. 9 is a method to treat lung adenocarcinoma in a patient in need of such treatment in accordance with an example embodiment.

Block 901 states determine a patient with lung adenocarcinoma. In an example embodiment, methods such as chest computerized tomography scan, sputum cytology, bronchoscopy, positron emission tomography scan, etc., can be used to determine whether a patient has lung adenocarcinoma.

Block 902 states administer the compound of formula I to the patient to treat the lung adenocarcinoma. In one example embodiment, the compound is administered directly or in pharmaceutical compositions along with suitable carriers or excipients. In one example embodiment, suitable routes of administration may, for example, include oral, rectal, transmucosal, nasal, or intestinal administration and parenteral delivery. The compound or the pharmaceutical composition that includes the compound can be administered locally. For example, the compound can be delivered via injection or in a targeted drug delivery system, such as a depot or sustained release formulation.

As used herein, the term "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "therapeutically effective amount" refers to any amount of a compound which, as compared to a corresponding patient who has not received such amount, results in improved treatment, healing, prevention, or amelioration of a disease, disorder, or side effect, or a decrease in the rate of advancement of a disease or disorder.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "administration" or "administering" of the patient compound refers to providing a compound of an example embodiment and/or prodrugs thereof to a patient in need of treatment.

What is claimed is:

1. A method of treating non-small cell lung cancer (NSCLC) in a patient, comprising:
    administering a therapeutically effective amount of a compound to the patient to treat the NSCLC,
    wherein the compound is represented by formula I

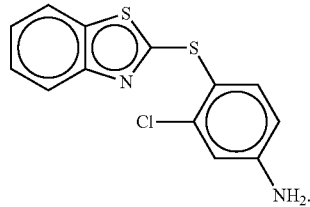

formula I

2. The method of claim 1, wherein cells of the NSCLC express a mutant Kirsten rat sarcoma 2 viral oncogene homolog (KRAS).

3. The method of claim 2, wherein the mutant KRAS includes an amino acid substitution from a glycine to a cysteine at codon 12 or a glutamine to a histidine at codon 61.

4. The method of claim 2, wherein the mutant KRAS includes amino acid substitution from a glycine to a cysteine at codon 12 and a glutamine to a histidine at codon 61.

5. The method of claim 2, wherein the mutant KRAS causes an increased level of guanosine triphosphate (GTP)-bound KRAS, and the compound inhibits the level of GTP-bound KRAS to treat the NSCLC.

6. The method of claim 2, where the mutant KRAS activates phosphorylation of CRAF, and the compound inhibits the phosphorylation of the CRAF to treat the NSCLC.

7. A method of treating lung adenocarcinoma in a patient in need of treatment of the lung adenocarcinoma, comprising:
    administering a therapeutically effective amount of a compound to the patient to treat the lung adenocarcinoma, wherein the compound is represented by formula I

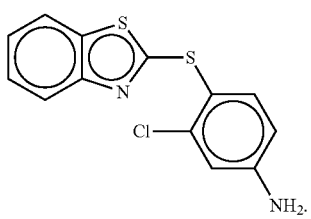

formula I

8. The method of claim 7, wherein tumor cells of the lung adenocarcinoma have a mutant Kirsten rat sarcoma 2 viral oncogene homolog (KRAS).

9. The method of claim 8, wherein the mutant KRAS includes an amino acid substitution from a glycine to a cysteine at codon 12 or a glutamine to a histidine at codon 61.

10. The method of claim 8, wherein the mutant KRAS includes amino acid substitution from a glycine to a cysteine at codon 12 and a glutamine to a histidine at codon 61.

11. The method of claim 8, wherein the compound inhibits an increased level of guanosine triphosphate (GTP)-bound KRAS that is caused by the mutant KRAS so that the lung adenocarcinoma is treated.

12. The method of claim 8, where the mutant KRAS activates phosphorylation of CRAF, and the compound inhibits the phosphorylation of the CRAF to treat the lung adenocarcinoma.

13. The method of claim 7, wherein the patient has non-small cell lung cancer.

14. A method of inhibiting progress of tumor growth in a patient with cancer, comprising:
diagnosing the patient with the cancer when the presence of a mutation of Kirsten rat sarcoma 2 viral oncogene homolog (KRAS) in cancer cells is detected; and
administering a compound to the patient with the cancer to inhibit the progress of tumor growth,
wherein the compound is represented by formula I

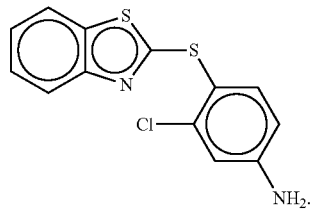

formula I

15. The method of claim 14, wherein the mutation of KRAS includes an amino acid substitution from a glycine to a cysteine at codon 12 or a glutamine to a histidine at codon 61.

16. The method of claim 14, wherein the mutation of KRAS includes amino acid substitution from a glycine to a cysteine at codon 12 and a glutamine to a histidine at codon 61.

17. The method of claim 14, wherein the compound inhibits an increased level of guanosine triphosphate (GTP)-bound KRAS that is caused by the mutation of KRAS so that the cancer is treated.

18. The method of claim 14, wherein the mutation of KRAS activates phosphorylation of CRAF, and the compound inhibits the phosphorylation of the CRAF to treat the cancer.

19. The method of claim 14, wherein the patient has non-small cell lung cancer.

20. The method of claim 14, wherein the patient has lung adenocarcinoma.

\* \* \* \* \*